(12) United States Patent
Hislop (10) Patent No.: US 12,263,112 B2
(45) Date of Patent: Apr. 1, 2025

(54) FINGER SUPPORTS AND GLOVES INCORPORATING THE SAME

(71) Applicant: Neil Shaka Hislop, Concord, MA (US)

(72) Inventor: Neil Shaka Hislop, Concord, MA (US)

( * ) Notice: Subject to any disclaimer, the term of this patent is extended or adjusted under 35 U.S.C. 154(b) by 465 days.

(21) Appl. No.: 17/510,651

(22) Filed: Oct. 26, 2021

(65) Prior Publication Data

US 2022/0039983 A1    Feb. 10, 2022

Related U.S. Application Data

(63) Continuation-in-part of application No. 15/990,017, filed on May 25, 2018, now abandoned, which is a continuation of application No. PCT/US2016/063800, filed on Nov. 27, 2016.

(60) Provisional application No. 62/260,566, filed on Nov. 29, 2015, provisional application No. 62/410,423, filed on Oct. 20, 2016.

(51) Int. Cl.
*A61F 5/01*    (2006.01)

(52) U.S. Cl.
CPC ...... *A61F 5/013* (2013.01); *A61F 2005/0144* (2013.01); *A61F 2005/0172* (2013.01)

(58) Field of Classification Search
CPC .. A61F 5/013; A61F 5/05875; A61F 5/05866; A61F 5/058; A61F 5/0118; A61F 13/105; A61F 13/104; A63B 2209/10; A63B 23/16; A63B 71/141; A63B 71/143; A63B 71/148; A41D 19/00; A41D 19/0017; A41D 19/015; A41D 19/01582; A41D 19/01588
USPC ...... 128/846, 869, 878, 879, 880; 602/5, 20, 602/21, 22, 30
See application file for complete search history.

(56) References Cited

U.S. PATENT DOCUMENTS

| | | | | |
|---|---|---|---|---|
| 8,702,635 | B2 * | 4/2014 | Hegland | A61F 5/05875 602/22 |
| 2009/0172864 | A1 * | 7/2009 | Fisher | A63B 71/148 2/163 |
| 2013/0338556 | A1 * | 12/2013 | Hoffman | A63B 21/0421 602/22 |

* cited by examiner

*Primary Examiner* — Caitlin A Carreiro
(74) *Attorney, Agent, or Firm* — Louis J. Franco; Law Office of Louis J. Franco (57) ABSTRACT

A finger brace is configured for disposition about a lengthwise portion of a human finger between a brace proximal and distal ends. When installed for bracing, the proximal end is anchored at least partially about the outer side of the finger at a location behind the PIP joint. The distal end includes a shank configured for coextension along a lengthwise portion of the outer side of the finger between the PIP joint and the finger nail. Situated between and connecting the support proximal and distal ends is a PIP-joint support that at least partially encircles and supports the PIP joint. In various configurations, a finger brace is incorporated into each glove finger of a sports glove to define a larger overall finger support system. The shanks may be articulated to promote finger bending while preventing rearward hyperextension.

18 Claims, 4 Drawing Sheets

FINGER SUPPORTS AND GLOVES INCORPORATING THE SAME

CROSS-REFERENCE TO RELATED APPLICATION/PRIORITY CLAIMS

The present application is a continuation-in-part of U.S. application Ser. No. 15/990,017 filed May 25, 2018 under the title "FINGER SUPPORTS AND GLOVES INCORPORATING THE SAME." application Ser. No. 15/990,017 with the present application on the date the present application was filed.

Previous application Ser. No. 15/990,017 was filed as a continuation of International Application Serial No. PCT/US2016/063800 filed Nov. 27, 2016 pursuant to the Patent Cooperation Treaty, and under the title "FINGER SUPPORTS AND GLOVES INCORPORATING THE SAME." Application PCT/US2016/063800 claimed priority benefits in U.S. Provisional Application No. 62/260,566 filed Nov. 29, 2015 under the title "PROXIMAL INTERPHALANGEAL JOINT AND COLLATERAL LIGAMENT FINGER SUPPORT," as well as Provisional Application No. 62/410,423 filed Oct. 20, 2016 under the title "SPORTS GLOVE WITH ARTICULATED FINGER SUPPORTS."

The present application claims the benefit of the filing dates of Provisional Application Ser. Nos. 62/260,566 and 62,410,423, as well as the filing date of PCT Application No. PCT/US2016/063800 and the filing date of U.S. application Ser. No. 15/990,017, based on the priority chain outlined above. Moreover, the entireties of the disclosures, including the drawings, of all four previous applications in the aforesaid priority chain are incorporated herein by reference as if set forth fully in the present application.

BACKGROUND

Injuries to the fingers of the hand can substantially limit mobility and dexterity. Moreover, continued use of injured fingers without proper support can exacerbate pain, as well as joint, tendon and tissue damage. These realities are compounded among persons who rely heavily on their hands for work or recreation. Among this group are, for example, landscapers, construction workers, and athletes of all levels, from recreational to professional.

A common finger injury among certain athletes is hyperextension resulting from the rearward being of the finger beyond its natural range of motion. Among the measures taken by athletes to prevent initial or further finger injury of already-injured fingers is the wrapping of fingers in tape. For more severe injuries, a finger might be secured to a splint with athletic tape. Even taping substantially limits mobility, and is nevertheless a is time-consuming process that must be repeated before practices and games. Splinting is a less temporary measure, but results in very limited mobility.

Accordingly, there exists a need for a finger brace and associated finger support system that can be readily installed about one or more fingers, adjusted, removed and reinstalled, while allowing an acceptable range of finger motion required for task performance.

SUMMARY

Broadly, each of various embodiments of a finger brace is configured for disposition about and along a lengthwise portion of a human finger including an outer side, an inner side, a PIP (proximal interphalangeal) joint and a fingertip bearing a finger nail. The outer and inner sides of the finger correspond to, respectively, the finger-nail and palm-side of the finger. It should also be noted that "outer side of the finger" and "inner side of the finger" are alternatively referred to as, respectively, "finger outer side" and "finger inner side." These are just two examples in which alternative expressions may be used to refer to the same component or element; context will render such circumstances and uses apparent, but use of one is to be regarded as sufficient antecedent basis for the other when clearly referring to the same element or object.

The finger brace has a brace proximal end, a brace distal end, an elongated finger-supporting shank, and a PIP-joint support. The brace proximal end is configured for situating at least partially about the finger at a location behind (rearward of) the PIP joint and on the finger outer side. The longitudinally opposed brace distal end includes an elongated shank (i.e., at least a portion of an elongated shank) configured for coextension along a lengthwise portion of the finger outer side between the PIP joint and the finger nail. The PIP-joint support extends between and connects the support proximal and distal ends, and is configured to at least partially encircle and support the PIP joint while allowing the PIP joint to bend.

For purposes of establishing orientation and relative spatial arrangements of finger brace elements and portions of the human hand and fingers, a first element or finger portion is regarded as "rearward of" or "behind" a second element or finger portion if that first element or finger portion is closer to the wrist of the hand being referenced than is the second element or finger portion. Correlatively, a second element or finger portion that is closer to the finger tip or finger nail than is a first element is regarded as "forward of" or "in front of" that first element. "Proximal' and "distal" are similarly defined such that, for example, any of the "joints" or "knuckles" of a finger is considered more proximal than is the finger nail of that finger because the joint is closer to the wrist than is the finger nail. These definitions are, in fact, consistent with the identification of interphalangeal joints in anatomy and medical books. More specifically, the distal interphalangeal joints (i.e, DIP joints) of the fingers are defined as those joints closest to the finger nails, while the proximal interphalangeal joints (i.e., PIP joints) are those joints situated "rearwardly" of the PIP joints; that is, the PIP joints are closer to the metacarpals (hand bones) and wrist and farther from the fingernails than are the DIP joints.

In each of various embodiments, the finger brace is fabricated from a material that is sufficiently rigid to be self-supporting, but which also exhibits an elastic property and "memory" that allows is to be flexed under a flexing force and then, when the flexing force is removed, return to a default configuration. A non-limiting set of illustrative materials includes (i) elastomeric plastics/polymers, (ii) rubberized materials, (iii) deformable "rigid" gels such as those found in some sports mouthguards, and (iv) silicone, such as medical grade silicon. Some elasticity in the material is desirable not only to allow flexing of the braced finger, but to provide a somewhat "snug" fit about the PIP joint inserted into the PIP-joint support portion. The shank is more rigid than the PIP-joint support in various versions, but may also by comprised of at least one of (i) elastomeric plastics/polymers, (ii) rubberized materials, (iii) deformable "rigid" gels such as those found in some sports mouthguards, and (iv) silicone, such as medical grade silicon, or even leather or metal, is by way of non-limiting example. Moreover, as the term "shank" connotes, unless otherwise defined to the contrary, the elongated shank is a single, unitary or "continuous" structure, although it may exhibit a degree of flexibility. Accordingly, where, within the ordinarily understood meaning of "shank," the elongated shank is a single, unitary structure, it is not comprised, for example, of a plurality of discrete, interconnected (e.g., assembled) elements.

Irrespective of the material from which the finger brace is fabricated, in at least one variation, the PIP-joint support comprises opposing helical first and second bands. The first and second bands are configured such that, when the finger brace is properly installed about the finger, the bands cooperate to provide PIP-joint support. More specifically, each of the first and second bands encircles at least a portion of the finger. The first and second bands cross one another at a band-crossing point located to the inside of the PIP joint on the palm side of the hand (i.e., the finger inner side). Moreover, as viewed from a lateral finger side, the first and second bands mutually diverge away from the band-crossing point and toward the finger outer side on the non-palm-side of the hand to locations situated behind and forward of the PIP joint.

The two-band PIP-joint support is illustrative only of a particularly advantageous configuration. Accordingly, it is to be explicitly understood that the invention is not so limited in scope except to the extent that express claims language so limits particular embodiments of same. In one alternative configuration, the PIP-joint support is simply a sleeve, loop or ring of material that encircles the finger and extends over the PIP joint between locations rearward and forward of the PIP joint. In another configuration, the PIP-joint support could comprise two such finger-encircling sleeves, loops or rings that do not cross one another, one rearward of the PIP joint and the other forward thereof. Still another possibility within the scope of broader inventive aspects is a two-band configuration in which first and second bands cross one another twice, once on each of the two finger lateral sides such that, as viewed from a side, the first and second bands resemble an "X."

In each of various alternative embodiments, a finger brace is incorporated into each of one or more glove fingers of a glove in order to define an overall finger support system. In one such embodiment, a glove finger is configured for insertion of a corresponding human finger with the finger brace installed about the finger. The glove finger has glove-finger interior and exterior surfaces and defined therethrough a transverse opening or slot (an opening/slot that has a lateral component of spatial extension across the glove finger) through which the shank of the finger brace protrudes for disposition to the glove-finger exterior along the finger outer side, forward of the PIP joint, with a portion of the glove finger situated between the shank and the finger outer side. The protrusion of the shank to the exterior of the glove finger facilitates a user's adjustment of the finger brace about the finger by means of the shank without requiring removal of the glove.

In alternative versions in which the shank of a finger brace protrudes to the exterior of a corresponding glove finger, the shank may be secured to the glove-finger exterior surface. In accordance with some alternative versions, the securement is temporary. Illustrative, non-limiting methods of temporary securement are achieved through at least one of (i) tape, (ii) an elastic band, and (iii) a plurality of hook-and-loop fasteners. In other versions, the securement of the shank to the glove-finger exterior is permanent and may be achieved through the use of at least one of (i) stitching, (ii) adhesive, such as glue or epoxy, (iii) heat fusion and (iv) snap-fitting (e.g., riveting), by way of non-limiting example.

As a general observation relative to various alternative embodiments, the elongated shank has a shank outside surface and a shank inside surface opposite the shank outside surface. When disposed along the finger outer side as intended, the shank inside surface is more proximate the finger outer side than is the shank outside surface. In at least one version, the elongated shank is articulated such that the shank outside surface is defined by a plurality of mutually adjacent armor segments separated by grooves. More specifically, while the elongated shank is overall a unitary structure, and the shank inside surface is "continuous," the shank outside surface has defined therealong a plurality of grooves and, relative to the grooves, raised armor segments. In the course of fabrication, the grooves may be cut, molded, pressed, etched, or otherwise imparted to a continuous and elongated substrate of material from which the elongated shank is formed.

Each armor segment includes an outwardly-facing segment top surface and segment front and rear surfaces, each of which segment front and rear surfaces defines a portion of one of the grooves separating the armor segment of which it forms a part from an adjacent armor segment. The armor segments and grooves are configured and mutually situated such that the finger supported by the shank can bend forward toward the palm but is prevented from bending backward beyond a predetermined extent by action of the mutual contacting engagement of the segment front and rear surfaces of neighboring armor segments. Thusly configured, the shank guards against rearward hyperextension of the finger supported thereby.

Regardless of the particular shank configuration, in each of various embodiments, a finger brace is structurally incorporated into an overall finger support system that further comprises a glove including a plurality of glove fingers. Each glove finger is configured for insertably receiving a human finger and has glove-finger interior and exterior surfaces. The glove-finger exterior surface defines glove-finger upper and lower surfaces corresponding to, respectively, the outer and inner sides of a human finger inserted therein. In a broad configuration, at least one the glove fingers carries the finger brace such that at least the shank of the finger brace is disposed along the outer side of the human finger. However, envisioned within the scope of the invention are practical implementations in which each of at least the four glove fingers corresponding to all fingers of the human hand other than the thumb carriers a finger brace. In still additional embodiments, the glove finger configured for receiving the thumb also carrier a finger brace.

Included among the alternative uses of variously embodied finger braces and finger support systems within the scope of the invention is the prevention of initial injury to the fingers of an athlete. Additionally or alternatively, embodiments may be implemented to support one or more fingers of an athlete recovering from finger injury. Although the invention was conceived with soccer goaltenders in mind, it will be appreciated that alternative configurations of the same may find broader utility among players of American-style football, golf, baseball, hockey, lacrosse, field hockey, and racquet sports of all types, by way of non-limiting example. Still further application may be found among members of the public more generally.

Representative embodiments are more completely described and depicted in the following detailed description and the accompanying drawings.

DETAILED DESCRIPTION

The following description of variously embodied proximal interphalangeal joint and collateral ligament finger supports, and sports gloves incorporating the same, is demonstrative in nature and is not intended to limit the invention or its application of uses. Accordingly, the various implementations, aspects, versions and embodiments described in the summary and detailed description are in the nature of non-limiting examples falling within the scope of the appended claims and do not serve to restrict the maximum scope of the claims. Moreover, among the various depicted embodiments, like reference numbers are used to refer to similar or analogous components.

Figure 1:
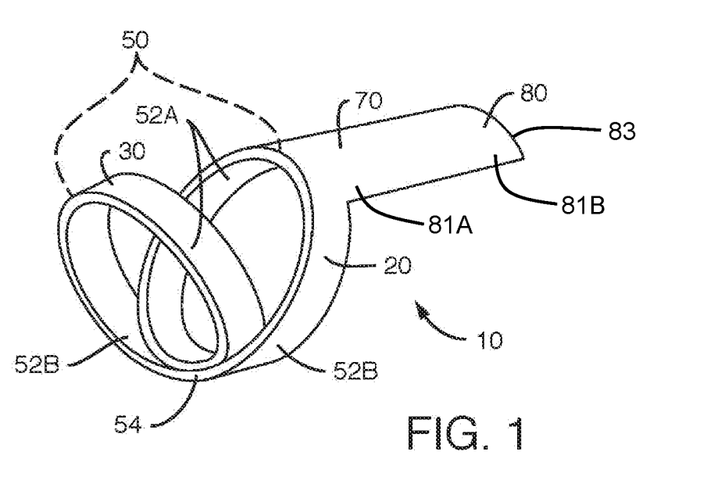
FIG. 1 is a right-rear side perspective view of a finger brace shown in isolation from a finger to be braced.
Figure 2:
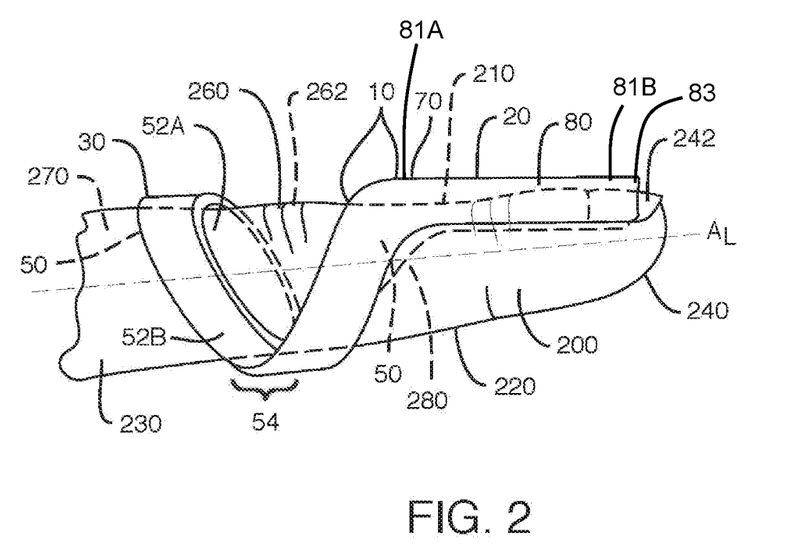
FIG. 2, is a right-side view of a finger brace such as that of FIG. 1 installed about a human finger to support the same.
Figure 3:
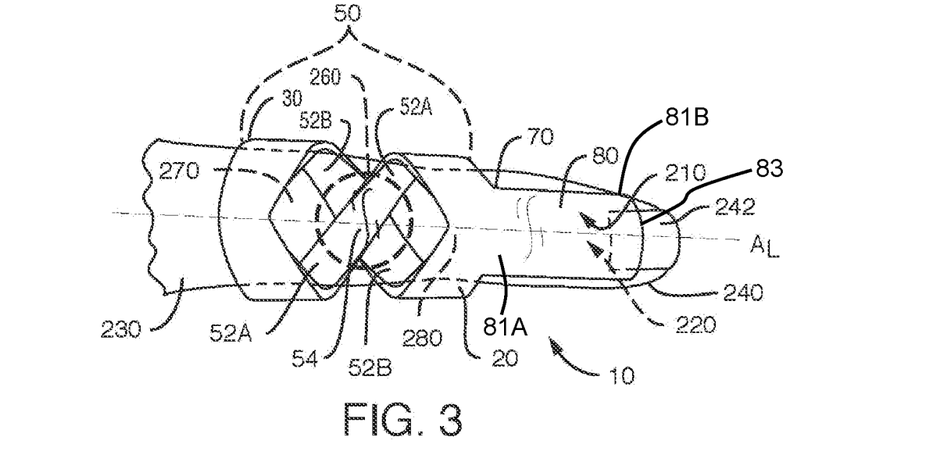
FIG. 3 is a top-side view of the finger and finger brace shown in FIG. 2.

Referring initially to FIGS. 1-3, various views of a proximal interphalangeal joint and collateral ligament finger support 10 are shown. For the sake of brevity and simplicity, a proximal interphalangeal joint and collateral ligament finger support 10 may be alternatively referred to as "finger support" throughout the summary and detailed description, as well as the claims. Additionally, the proximal interphalangeal joint is alternatively referred to as the "PIP joint."

A first embodiment of a finger support 10 includes a finger brace 20 configured for disposition about and along a lengthwise portion of a human finger 200, the lengthwise extent of which is indicated by longitudinal axis $A_L$ in each of FIGS. 2 and 3. For purposes of establishing referential spatial orientations within the environment of use, the finger 200 is regarded as including an "upper" or finger outer side 210 corresponding to the finger-nail side of the finger 200, and a "lower" or finger inner side 220, opposite the finger outer side 210, and corresponding to the palm-side of the hand. Additionally, as one would expect, the lengthwise extent of the finger 200 is defined to extend between a finger proximal end 230 that is closest the main portion of the hand including the palm (not shown) and a finger distal end 240 (alternatively, "fingertip 240") that includes the finger nail 242. As shown in FIG. 2, the PIP joint 260 is the joint—or knuckle—situated between the first (also called proximal) and second (intermediate) phalanges 270 and 280 of the finger 200.

Returning now to the finger brace 20, a brace proximal end 30 is configured for situating at least partially about the finger 200 at a location that is both behind the PIP joint 260 and at least on the finger outer side 210 of the finger 200. A brace distal end 70 includes an elongated shank 80 (alternatively referred to as "shank 80") configured for coextension along a lengthwise portion of the finger outer side 210 forward of the PIP joint 260. For example, when one version of the finger brace 20 is properly installed about the finger 200, the elongated shank 80 extends between the PIP joint 260 and the finger nail 242. Extending between and connecting the brace proximal end 30 to the brace distal end 70 is a PIP-joint support 50 which is configured to at least partially encircle and support the PIP joint 260 while allowing the PIP joint 260 to bend. The elongated shank 80 extends forwardly from a shank rearward end 81A to a shank forward end 81B, the latter of which terminates at and defines a distal shank tip 83. Consistent with the definitions of terms such as "rearward," "proximal," "forward," and "distal" indicated in the summary, when the finger brace 20 is properly installed about the finger 200, the shank forward end 81B and the shank tip 83 are more proximate the wearer's finger nail 242 than is the shank rearward end 81A.

The specific version of the PIP-joint support 50 shown in FIGS. 1-3 includes "opposing" helical first and second bands 52A and 52B. The helical first and second bands 52A and 52B are "opposing" or "opposed" in the sense that one of the bands 52A and 52B is a "right-handed helix," while the other is a "left-handed helix." Moreover, the helical first and second bands 52A and 52B at least partially co-extend along the longitudinal axis $A_L$ and are cooperatively configured such that, when the finger brace 20 is properly installed about the finger 200, (i) each of the first and second helical bands 52A and 52B encircles at least a portion of the finger 200; (ii) the first and second bands 52A and 52B cross one another at a band-crossing point 54 located to the inside of the PIP joint 260 on the palm side of the hand; and (iii) as viewed from a side, the first and second bands 52A and 52B mutually diverge away from the band-crossing point 54 on the finger inner side 220 and to locations situated on the finger outer side 210 behind and forward of the PIP joint 260.

Still more specifically, the first and second bands 52A and 52B cooperate to form a PIP-joint support 50 that, when viewed from a side, as in FIG. 2, resembles a "V" and, when viewed from the top, as in FIG. 3, resembles a "figure 8." The PIP joint 260 is supported from underneath, at or near, the "bend point" 262 of the knuckle by the crossing first and second bands 52A and 52B, while, on the finger outer side 210, the PIP joint 260 is supported forward and rearward of the bend point 262. On the upper, finger outer side 210, the bend point 262 of the PIP joint 260 is not covered by any portion of the PIP-joint support 50 of the present embodiment, an aspect that facilitates bending of the finger 200 at the PIP joint 260. On the lateral sides of the finger 200 (between the finger outer and inner sides 210 of 220), the PIP joint 260 is laterally supported mostly forward of and rearward of the bend point 262 until, near the very bottom of the "V," the first and second bands 52A and 52B converge toward their crossing location 54 on the underside of the knuckle on and along the finger inner side 220.

Figure 4:
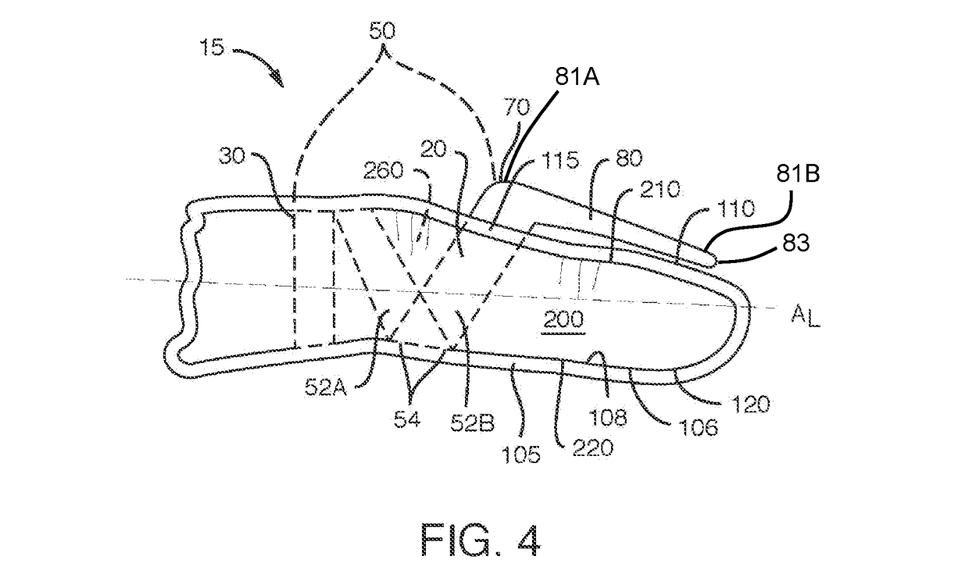
FIG. 4 is a partial right-side view of a finger support system cooperatively incorporating a finger brace such as that of FIGS. 1-3 and a glove finger disposed about a finger being braced thereby.

Although, as indicated above, and in FIGS. 1-3, the finger brace 20 can be used as a stand-alone support device, alternative implementations call for its incorporation into a finger support system 15 that further includes a glove. More specifically, with reference to the cross-sectional view of FIG. 4, a glove finger 105 is configured for insertably receiving a human finger 200 and the finger brace 20 installed about the finger 200. The glove finger 105 includes glove-finger exterior and interior surfaces 106 and 108. Glove-finger upper and lower surfaces 110 and 120 extend along the exterior of the glove finger 105 and correspond, respectively, to the finger outer and inner sides 210 and 220 of a human finger 200 inserted therein. Since they are defined to extend along the exterior of the glove finger 105, the glove-finger upper and lower surfaces 110 and 120 can be regarded as sub-surfaces or surface portions of the glove-finger exterior surface 106.

The glove finger 105 has defined therethrough a transverse opening 115 (e.g., incision, slit or slot) situated and configured to accommodate the protrusion to the exterior of the glove finger 105 of the shank 80 of the finger brace 20 therefrom. More specifically, when the finger brace 20 is properly installed about the finger 200, and the glove is disposed over the hand, the PIP-joint support 50 is situated to the interior of the glove finger 105, while the shank 80 of the finger brace 20 protrudes through and forwardly from the transverse opening 115 for disposition along the glove-finger upper surface 110 and the finger outer side 210 forward of the PIP joint 260 with a portion of the glove finger 105 situated between the shank 80 and the finger outer side 210. The protrusion of the shank 80 of the finger brace 20 facilitates a user's adjustment of the finger brace 20 about the finger 200 by means of the shank 80 without requiring removal of the glove from the hand. It will be readily appreciated from the preceding description, as well as examination of at least FIG. 4, that it is at least a forward portion of the elongated shank 80, including the shank forward end 81B and the shank tip 83, that is protrudes through and forwardly from the transverse opening 115 for situational disposition more proximate the finger nail 242 than the shank rearward end 81A.

In alternative implementations of a finger support system 15 cooperatively incorporating both a finger brace 20 and a glove finger 105, the shank 80 of the finger brace 20 is secured to the glove-finger exterior along the glove-finger upper surface 110. In some instances, the shank 80 is permanently secured to the glove-finger upper surface 110 while, in other instances, the shank 80 may be temporarily secured to the glove-finger upper surface 110. Temporary securement may be achieved, by way of non-limiting example, through the use of at least one of (i) adhesive tape, (ii) an elastic band and (iii) a plurality of hook-and-loop fasteners, such as those most commonly marketed under the tradename "Velcro®".

In still additional implementations, a finger support system 15 includes a glove-finger 105 and finger brace 20 cooperatively preconfigured such that the shank 80 of the finger brace 20 protrudes through a transverse opening 115 in the glove finger 105 and extends along the glove-finger upper surface 110. Moreover, the finger brace 20 is secured to at least one of the glove-finger exterior interior surfaces 106 and 108 with the PIP-joint support 50 aligned and oriented within the glove finger 105 such that the glove can be placed on a user's hand and the finger 200 to be braced inserted into the proximal end 30 of the finger brace 20 until the PIP joint 260 is situated for support within the PIP-joint support 50. In other words, in a preconfigured embodiment of this latter type, the glove finger 105 and finger brace 20 are joined and provided as a pre-assembled single, cooperatively-functioning unit into which a user inserts his or her finger 200 as the glove of which the glove finger 105 and finger brace 20 are an integral part is pulled onto the user's hand. This is distinguishable from scenarios in which a user first installs the finger brace 20 about the finger 200 to be braced and then, subsequently, inserts the already-braced finger 200 into the glove finger 105.

Although embodiments of finger support systems 15 including both a finger brace 20 and a glove finger 105 are depicted and described principally with reference to a single one of each of (i) a finger 200 to be braced, (ii) a finger brace 20, and (iii) a glove finger 105, it is to be understood that finger support systems 15 incorporating a plurality of finger braces 20 carried by a corresponding plurality of glove fingers 105 of a single glove are expressly within the scope and contemplation of the invention.

Figure 5:
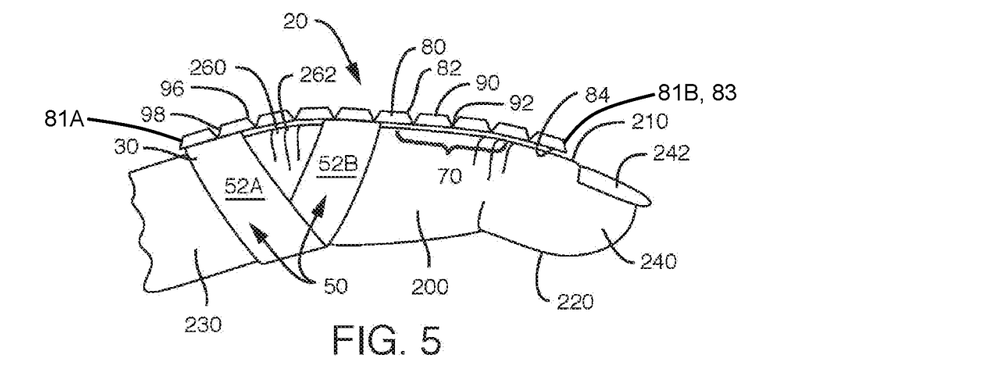
FIG. 5 is a right-side view of a finger brace with an articulated shank installed about a human finger for support of same.

Referring now to the side view of FIG. 5, an alternatively configured finger brace 20 is shown and described. In several key respects, the finger brace 20 of FIG. 5 is configured similarly to those of FIGS. 1 through 4 and, to the extent that is true, like reference characters are used to reference correspondingly similar elements. As previously described, the finger brace 20 is configured for disposition about and along a lengthwise portion of a human finger 200 including a finger outer side 210, a finger inner side 220, a PIP joint 260 and a fingertip 240 bearing a finger nail 242. Since components and elements of the finger brace 20, and their relative positions as "forward," "rearward," "inner," "outer," etc. are best understood with reference to the environment in which the finger brace 20 is properly situated on a human finger 200, the finger brace 20 is thusly shown and described, unless otherwise noted or rendered obvious by context.

The finger brace 20 includes a brace proximal end 30 situated at least partially about the human finger 200 at a location behind the PIP joint 260 and on the finger outer side 210. Extending forwardly of the brace proximal end 30 toward the fingertip 240 is a brace distal end 70. As with the versions previously described, the finger brace 20 presently under consideration includes a PIP-joint support 50 extending between the brace proximal and distal ends 30 and 70. Additionally, the PIP-joint support 50 is configured to at least partially encircle and support the PIP joint 260 while allowing the PIP joint 260 to bend.

While the version of FIG. 5 also includes an elongated shank 80 coextending with a lengthwise portion of the finger outer side 210 between the PIP joint 260 and the finger nail 242, there are notable differences between the present version and that of FIGS. 1 through 4. Most notably, the elongated shank 80 of FIG. 5 is articulated. More specifically, the elongated shank 80 which, like the shanks 80 of previously disclosed configurations, includes a shank outside surface 82 and a shank inside surface 84 opposite the shank outside surface 82 and more proximate the finger outer side 210 than is the shank outside surface 82. However, while the shank 80 is a unitary and continuous structure, the shank outside surface 82 is defined by (or defines) a plurality of mutually adjacent armor segments 90 (alternatively, "ridges") separated by grooves 92.

Figure 5A:
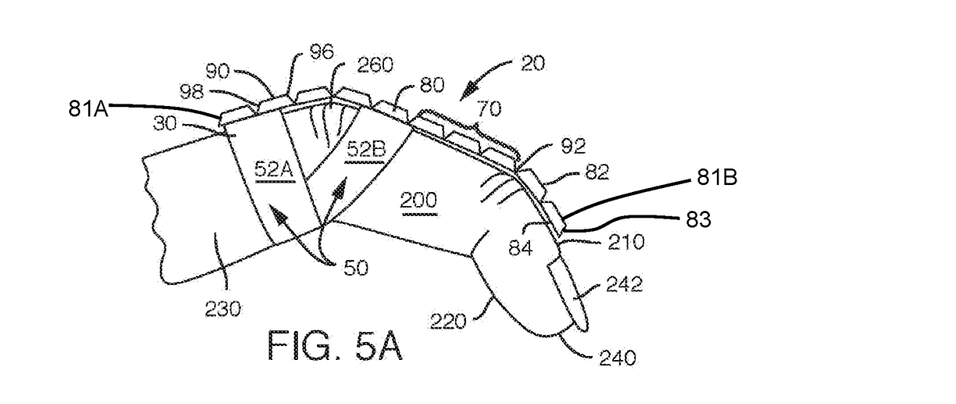
FIG. 5A shows the finger and finger brace of FIG. 5 with the supported finger in a bent attitude.
Figure 5B:
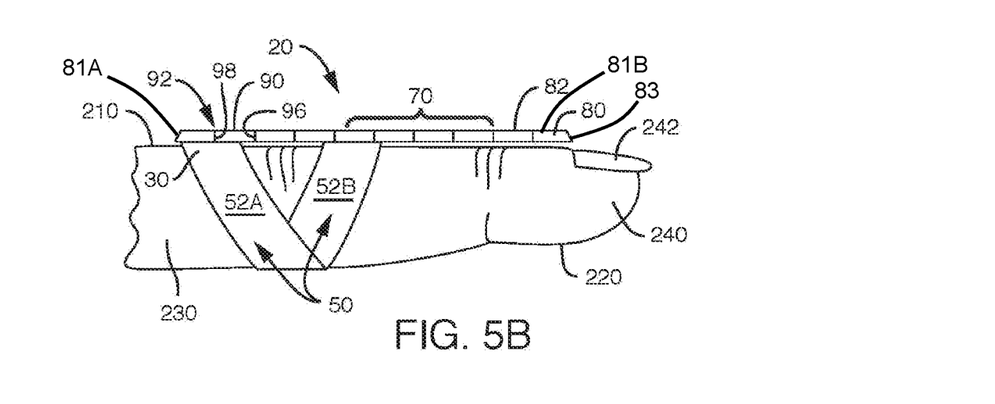
FIG. 5B depicts how the finger brace with articulated shank of FIGS. 5 and 5A prevents a supported finger about which it is situated from bending backward beyond a predetermined extent in order to guard against hyperextension of the supported finger.

With continued principal reference to FIG. 5, but also to FIGS. 5A and 5B, each armor segment 90 includes an outwardly-facing segment top surface 94 and segment front and rear surfaces 96 and 98. Moreover, each segment front and rear surface 96 and 98 defines a portion of one of the grooves 92 separating the armor segment 90 of which it forms a part from an adjacent armor segment 90. As shown in FIG. 5A, the armor segments 90 and grooves 92 are configured and mutually situated such that the finger 200 supported by the shank 80 can bend forward—or inward—toward the palm. Importantly, however, the configuration and relative locations of the armor segments 90 and groves 92 act to prevent the finger 200 from bending backward beyond a predetermined extent by action of the mutual contacting engagement of segment front and rear surfaces 96 and 98 of neighboring armor segments 90, as shown in FIG. 5.

Another notable difference between the version of FIGS. 5-5B and those of FIGS. 1-4 relates to the longitudinal extent of the shank 80 along a human finger 200. More specifically, in the version of FIGS. 5-5B, the shank 80 originates at the shank rearward end 81A from the brace proximal end 30 at a location behind (i.e., rearward of) the PIP joint 260. From the brace proximal end 30, the shank 80 extends forwardly over the PIP joint toward the finger nail 242 in proximity to which the shank 80 terminates at the shank forward end 81B and defines the extreme distal portion of the brace distal end 70. This configuration, by extending over the PIP joint 260, provides support and protection of the finger 200 over a greater length. It is to be appreciated that alternative versions including either the greater shank length or wherein the elongated shank 80 is articulated are within the scope and contemplation of the invention.

Figure 6:
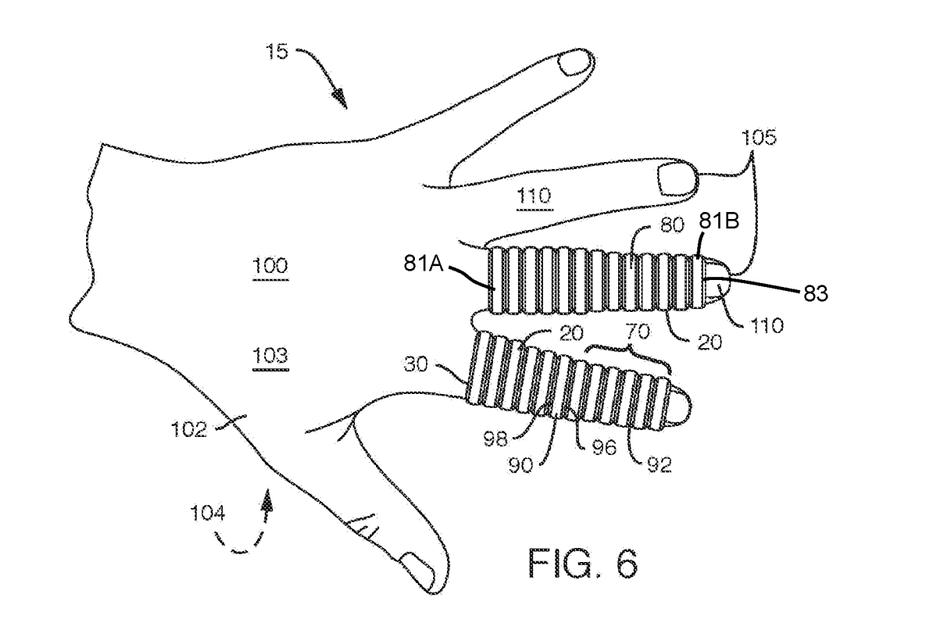
FIG. 6 is a top view of a finger support system including a glove having glove fingers into each of which there is incorporated a finger brace with a finger-supporting shank.

As with the versions of FIGS. 1-4, a version including an articulated shank 80 such as that of FIGS. 5-5B can be incorporated into a larger overall finger support system 15, and, more particularly, as shown in FIG. 6, a finger support system 15 in which at least one of the finger braces 80 is integrated within a glove 100 including a plurality of glove fingers 105. Although gloves 100 wherein each of the five glove fingers 105 includes a finger brace 20 having a shank 80—articulated or not—are contemplated and included within the claimed scope of the invention, the illustrative version of FIG. 6 depicts for descriptive purposes a glove 100 including only two such glove fingers 105. Additionally, FIG. 6A is a cross-sectional side view of one of the glove fingers 105 having an articulated shank 80 as shown in FIG. 6.

Figure 6A:
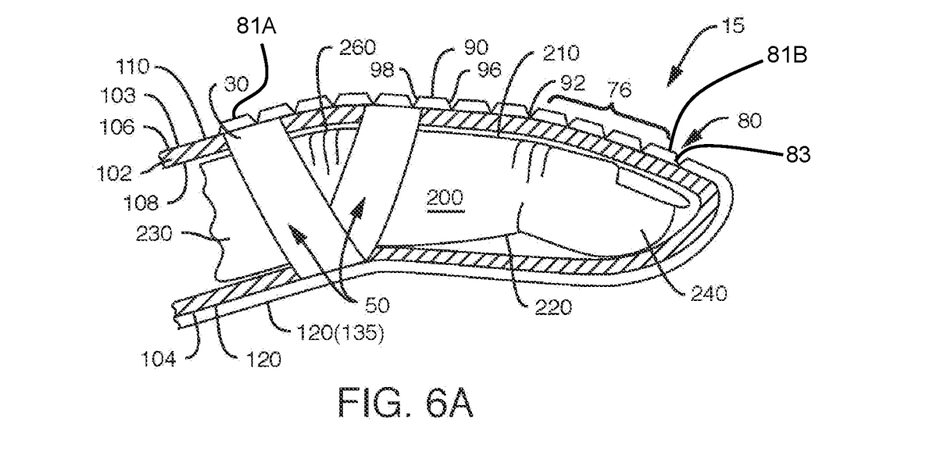
FIG. 6A is a cross-sectional side view of one of the glove fingers shown in FIG. 6.

With conjunctive reference to both FIGS. 6 and 6A, the glove 100 includes a glove-body wall 102, a glove-back side 103, and a glove-palm side 104. The glove-body wall 102 defines the glove-back and glove-palm sides 103 and 104 that extend over the main portion of a human hand as well as the glove fingers 105. As previously explained of single glove finger 105 in connection with alternative configurations of the finger brace 20, each glove finger 105 includes a glove-finger exterior and interior surfaces 106 and 108. Glove-finger upper and lower surfaces 110 and 120 extend along the exterior of the glove finger 105 and correspond, respectively, to the finger outer and inner sides 210 and 220 of a human finger 200 inserted therein. Since they are defined to extend along the exterior of the glove finger 105, the glove-finger upper and lower surfaces 110 and 120 can be regarded as sub-surfaces or surface portions of the glove-finger exterior surface 106. Also readily apparent is that the glove-back side 103 and glove-palm side 104 correspond to, respectively, the glove-finger upper and lower surfaces 110 and 120 of each of the plural glove fingers 105.

Referring principally to FIG. 6A, it will be appreciated that at least a portion of at least one of the elongated shank 80 and the PIP-joint support 50 is disposed along the glove-finger upper surface 110. In this case, the entirety of the shank 80 between the shank rearward and forward ends 81A and 81B is disposed along the glove-finger exterior surface 106, but it is to be understood that configurations in which all or part of the shank 80 are disposed internally (to the inside of glove-finger interior surface 108), or even encased within the glove-body wall 102 between the glove-finger exterior and interior surfaces 106 and 108, are within the scope of the appended claims except to the extent that explicit claim limitations to the contrary are recited.

Referring now to the PIP-joint support 50, in the example of FIG. 6A, the PIP-joint support 50 is disposed about the glove-finger exterior surface 106. However, it is to be understood that, as with the disposition of the shank 80, this is non-limitingly illustrative. As with the shank 80, the PIP-joint support 50 could be partially or entirely disposed about and to the inside of the glove-finger interior surface 108. Moreover, although configurations in which the PIP-joint support 50 is an element separately identifiable from the glove finger 105, included within the scope of the overall inventive concept is at least one embodiment in which the glove finger 105 itself is the PIP-joint support 50, with the elongated shank 80 being the only element of the finger brace 20 that is identifiable separately from the glove finger 105. In a case of the later type, for example, the PIP-joint support 50 does not include first and second bands 52A and 52B, but might otherwise appear generally similar to the example of FIG. 6A, whether or not the shank 80 is articulated.

As shown in the cross-sectional view of FIG. 6A, the glove 100 carrying one or more finger braces 20 may optionally further include an over-layer 130 of hand-protective padding 135 on at least the glove-palm side 104. Although only a cross-section of a glove finger 105 is shown in FIG. 6A, it is to be understood that, although not shown, the over-layer 130 may—and preferably does—extend over the glove-palm side 104 of the main body of the glove 100 as well. In the example of FIG. 6A, the over-layer 130 extends over the glove-finger lower surface 120, curves about the fingertip 240 of a wearer's finger 200 and meets the shank 80 on the glove-finger upper surface 110. Although the hand-protective padding 135 can be fabricated from various alternative materials, non-limiting examples include as least one of (i) foam, (ii) rubber, (iii) a polymeric material, (iv) genuine leather, (v) synthetic leather, and (vi) a gel.

The foregoing is considered to be illustrative of the principles of the invention. Furthermore, since modifications and changes to various aspects and implementations will occur to those skilled in the art without departing from the scope and spirit of the invention, it is to be understood that the foregoing does not limit the invention as expressed in the appended claims to the exact constructions, implementations and versions shown and described.

What is claimed is:

1. A finger brace configured for disposition about and along a lengthwise portion of a human finger including an outer side, an inner side, a PIP joint, and a fingertip bearing a finger nail, the finger brace, when properly situated on the finger, comprising:

a brace proximal end configured to be situated at least partially about the finger at a location behind the PIP joint and on the outer side of the finger;

a brace distal end configured to extend forwardly of the brace proximal end toward the fingertip;

a PIP-joint support extending between and connecting the brace proximal end and brace distal end, and configured to at least partially encircle and support the PIP joint while allowing the PIP joint to bend; and a unitary and continuous elongated shank configured to coextend along a lengthwise portion of the outer side of the finger between the PIP joint and the finger nail, the elongated shank having a shank outside surface and a shank inside surface opposite the shank outside surface and configured to be more proximate the outer side of the finger than the shank outside surface, wherein
  (a) the elongated shank is articulated such that the shank outside surface is defined by a plurality of mutually adjacent armor segments separated by grooves, each armor segment including an outwardly-facing segment top surface and segment front and rear surfaces, each of which segment front and rear surfaces defines a portion of one of the grooves separating an armor segment of which it forms a part from an adjacent armor segment; and
  (b) the armor segments and grooves are collectively configured and mutually situated such that the finger supported by the elongated shank can bend forward toward the palm but is prevented from bending backward beyond a predetermined extent by action of a mutual contacting engagement of the segment front and rear surfaces of neighboring armor segments.

2. The finger brace of claim 1 incorporated into a finger support system, the finger support system further comprising a glove including a plurality of glove fingers, each glove finger configured for insertably receiving a human finger and having glove-finger interior and exterior surfaces, the glove-finger exterior surface defining glove-finger upper and lower surfaces configured to correspond to, respectively, the outer and inner sides of a human finger inserted therein, wherein one of the glove fingers carries the finger brace such that at least the elongated shank of the finger brace is configured to be disposed along the outer side of the human finger.

3. The finger support system of claim 2, wherein at least a portion of at least one of the elongated shank and the PIP-joint support is disposed on the glove-finger exterior surface.

4. The finger support system of claim 3, wherein the glove finger is the PIP-joint support.

5. The finger support system of claim 3, wherein
  (i) the glove includes a glove-palm side and a glove-back side corresponding to, respectively, the glove-finger lower and upper surfaces of the plurality of glove fingers; and
  (ii) the glove-palm side and glove-finger lower surface has applied thereto an over-layer of hand-protective padding.

6. The finger support system of claim 5, wherein the hand-protective padding comprises at least one of (i) foam, (ii) rubber, (iii) a polymeric material, (iv) genuine leather, (v) synthetic leather, and (vi) a gel.

7. The finger brace of claim 2, wherein each of at least two of the glove fingers carries the finger brace such that at least the elongated shank of the finger brace is configured to be disposed along the outer side of the human finger insertably received by each of the at least two glove fingers.

8. The finger brace of claim 1, wherein the PIP-joint support comprises opposing helical first and second bands configured such that, when the finger brace is properly installed about the finger, the helical first and second bands mutually cooperate such that
  (i) each of the helical first and second bands is configured to encircle at least a portion of the finger;
  (ii) the helical first and second bands cross one another at a band-crossing point configured to be located to the inside of the PIP joint on the inner side of the finger; and
  (iii) as viewed from a side, the helical first and second bands are configured to mutually diverge away from the band-crossing point along a lengthwise portion of the finger and toward the outer side of the finger to locations situated on the outer side of the finger and behind and forward of the PIP joint.

9. The finger brace of claim 8, wherein the elongated shank originates from the brace proximal end at a location configured to be behind the PIP joint and is configured to extend forwardly over the PIP joint toward the finger nail.

10. The finger brace of claim 9 incorporated into a finger support system, the finger support system further comprising a glove including a plurality of glove fingers, each glove finger configured for insertably receiving a human finger and having glove-finger interior and exterior surfaces, the glove-finger exterior surface defining glove-finger upper and lower surfaces configured to correspond to, respectively, the outer and inner sides of a human finger inserted therein, wherein one of the glove fingers carries the finger brace such that at least the elongated shank of the finger brace is configured to be disposed along the outer side of the human finger.

11. The finger support system of claim 10, wherein at least a portion of at least one of the elongated shank and the PIP-joint support is disposed along the glove-finger upper surface.

12. A finger support system comprising:
  a finger brace configured for disposition about and along a lengthwise portion of a human finger including a finger outer side, a finger inner side, finger lateral sides, a PIP joint, and a fingertip bearing a finger nail, the finger brace including:
  (a) a brace proximal end configured for situating at least partially about the finger at a location behind the PIP joint and on the finger outer side;
  (b) a brace distal end including a unitary and continuous elongated shank configured for coextension along a lengthwise portion of the finger outer side between the PIP joint and the finger nail and having a shank rearward end and a shank forward end terminating in a distal shank tip configured for situational disposition more proximate the finger nail than is the shank rearward end; and
  (c) a PIP-joint support extending between and connecting the brace proximal end and brace distal end, and configured to at least partially encircle and support the PIP joint while allowing the PIP joint to bend; and
  a glove including a glove finger configured for insertion of the finger and the finger brace installed about the finger, the glove finger having glove-finger interior and exterior surfaces and defined therethrough an opening through which at least a portion of the elongated shank including the distal shank tip is configured to protrude for disposition to the glove-finger exterior surface along the finger outer side forward of the PIP joint with a portion of the glove finger configured to be situated between the elongated shank and the finger outer side, thereby facilitating a user's adjustment of the finger brace about the finger by means of the elongated shank without requiring removal of the glove.

13. The finger support system of claim 12, wherein the PIP-joint support comprises opposing helical first and second bands configured such that, when the finger brace is properly installed about the finger, the helical first and second bands mutually cooperate such that
  (i) each of the helical first and second bands is configured to encircle at least a portion of the finger;
  (ii) the helical first and second bands cross one another at a band-crossing point configured to be located to the inside of the PIP joint on the finger inner side; and (iii) as viewed from a lateral finger side, the helical first and second bands are configured to mutually diverge away from the band-crossing point and toward the non-palm-side of the hand to locations situated on the finger outer side and behind and forward of the PIP joint.

14. The finger support system of claim 13, wherein the elongated shank of the finger brace is secured to the glove-finger exterior surface one of (i) temporarily and (ii) permanently.

15. The finger support system of claim 14, wherein the elongated shank of the finger brace is secured temporarily to the glove-finger exterior surface by at least one of (i) tape, (ii) an elastic band, and (iii) a plurality of hook-and-loop fasteners.

16. The finger support system of claim 15, wherein the elongated shank of the finger brace is secured temporarily to the glove-finger exterior surface by at least one of (i) tape, (ii) an elastic band, and (iii) a plurality of hook-and-loop fasteners.

17. The finger support system of claim 13, wherein the finger brace is secured to at least one of the glove-finger interior and exterior surfaces and configured such that the PIP-joint support is aligned and oriented within the glove finger such that the glove can be placed on a user's hand, and the finger to be braced can be inserted into the brace proximal end, until the PIP joint is situated for support within the PIP-joint support.

18. The finger support system of claim 12, wherein the finger brace is secured to at least one of the glove-finger interior and exterior surfaces and configured such that the PIP-joint support is aligned and oriented within the glove finger such that the glove can be placed on a user's hand, and the finger to be braced can be inserted into the brace proximal end, until the PIP joint is situated for support within the PIP-joint support.

* * * * *